(12) United States Patent
Ales et al.

(10) Patent No.: US 8,044,363 B2
(45) Date of Patent: Oct. 25, 2011

(54) UV DETECTION DEVICES AND METHODS

(75) Inventors: Thomas Michael Ales, Neenah, WI (US); Richard Timmers, Bear, DE (US); Andrew Mark Long, Appleton, WI (US); Shawn Jeffrey Sullivan, Neenah, WI (US); Sridhar Ranganathan, Suwanee, GA (US); Timothy R. Obermann, Pulaski, WI (US); Eric Donald Johnson, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/799,044

(22) Filed: Apr. 30, 2007

(65) Prior Publication Data

US 2008/0265170 A1    Oct. 30, 2008

(51) Int. Cl.
*G01J 1/42* (2006.01)
(52) U.S. Cl. ............ 250/372; 250/336.1; 382/165; 382/116
(58) Field of Classification Search .......... 250/372, 250/336.1; 382/165, 116
See application file for complete search history.

(56) References Cited

U.S. PATENT DOCUMENTS

| | | | |
|---|---|---|---|
| 4,308,459 A | 12/1981 | Williams | |
| 4,348,664 A * | 9/1982 | Boschetti et al. | 340/600 |
| 4,528,986 A * | 7/1985 | Arundel et al. | 600/476 |
| 4,788,433 A | 11/1988 | Wright | |
| 4,882,598 A | 11/1989 | Wulf | |
| 4,962,910 A | 10/1990 | Shimizu | |
| 5,151,600 A * | 9/1992 | Black | 250/372 |
| 5,365,068 A | 11/1994 | Dickerson | |
| 5,581,090 A | 12/1996 | Goudjil | |
| 5,612,542 A | 3/1997 | Brown et al. | |
| 5,666,105 A * | 9/1997 | Adler et al. | 340/600 |
| 5,914,197 A | 6/1999 | Goudjil | |
| 5,986,273 A | 11/1999 | Tripp et al. | |
| 5,995,862 A * | 11/1999 | Gallorini | 600/407 |
| 6,046,455 A | 4/2000 | Ribi et al. | |
| 6,060,321 A | 5/2000 | Hovorka | |

(Continued)

FOREIGN PATENT DOCUMENTS

EP    0982572 A1    3/2000

(Continued)

OTHER PUBLICATIONS

Jablonski, Nina "Skin: A Natural History", University of California Press, 2006, pp. 68-69.*

(Continued)

*Primary Examiner* — David Porta
*Assistant Examiner* — Yara Green
(74) *Attorney, Agent, or Firm* — Dority & Manning, P.A.

(57) ABSTRACT

A portable UV detection apparatus is disclosed. In one embodiment, the UV detection apparatus includes a UV detection device integrated with a skin type measuring device. A controller can be included in the apparatus that is in communication with the skin type measuring device and the UV detection device. The controller can provide information to the user regarding the amount of ultraviolet radiation present in the environment. In an alternative embodiment, the UV detection apparatus includes a UV detection device in conjunction with a light sensor. The light sensor can be configured to activate the UV detection device should light at a particular intensity be present in the environment. The UV detection device as described above can be configured to measure UVA radiation, UVB radiation, and/or UVC radiation.

24 Claims, 4 Drawing Sheets

U.S. PATENT DOCUMENTS

| | | | |
|---|---|---|---|
| 6,130,435 A | 10/2000 | Rocklin | |
| 6,348,694 B1 * | 2/2002 | Gershteyn et al. | 250/372 |
| 6,405,867 B1 | 6/2002 | Moore | |
| 6,559,455 B2 | 5/2003 | Nash | |
| 6,698,590 B2 | 3/2004 | Moore | |
| 6,736,832 B2 * | 5/2004 | Lenderink et al. | 607/88 |
| 6,872,901 B2 * | 3/2005 | Su et al. | 200/61.02 |
| 6,936,824 B2 | 8/2005 | Takada | |
| 2003/0150998 A1 | 8/2003 | Shin et al. | |
| 2004/0031927 A1 | 2/2004 | Tsai et al. | |
| 2004/0109789 A1 | 6/2004 | Faran et al. | |
| 2004/0149921 A1 | 8/2004 | Smyk | |
| 2005/0067580 A1 | 3/2005 | Fontaine | |
| 2005/0133401 A1 | 6/2005 | Lange | |
| 2005/0145525 A1 | 7/2005 | Williams | |
| 2005/0230596 A1 | 10/2005 | Howell et al. | |
| 2005/0285050 A1 | 12/2005 | Bruce | |
| 2006/0204709 A1 | 9/2006 | Chen | |
| 2006/0210154 A1 | 9/2006 | Leveque et al. | |
| 2006/0226371 A1 | 10/2006 | Lu et al. | |

FOREIGN PATENT DOCUMENTS

| | | |
|---|---|---|
| EP | 1653204 A1 | 5/2006 |
| FR | 2822671 A | 10/2002 |
| GB | 2261504 A | 5/1993 |
| GB | 2408829 A | 6/2005 |
| WO | WO 9104469 A1 | 4/1991 |
| WO | WO 9610165 A1 | 4/1996 |
| WO | WO 0138836 A1 | 5/2001 |
| WO | WO2004/073326 * | 2/2004 |
| WO | WO 2005006758 A1 | 1/2005 |
| WO | WO 2005015138 A1 | 2/2005 |
| WO | WO 2005028505 A2 | 3/2005 |

OTHER PUBLICATIONS

Torigoe et al. Machine Translation of JP 2001-250966; published Sep. 2001.*

Article—Clarys et al. "Skin color measurements: comparison between three instruments: the Chromameter®, the Dermapectrometer®, and the Mexameter®." *Skin Research and Technology*. 6, 200: 230-238.

Article—Ha et al. "The Relationship Between Constitutive Pigmentation and sensitivity to Ultraviolet Radiation Induced Erythema is Dose-Dependent." *Pigment Cell Research*.16, 2003:477-479.

Article—Wagner et al. "Skin Responses to Ultraviolet Radiation: Effects id Pigmentation, Sex, and Ancestry." *Pigment Cell Research*. 15, 2002:358-390.

Partial International Search Report for Application No. PCT/IB2008/050804, mailed Jul. 10, 2008.

* cited by examiner

UV DETECTION DEVICES AND METHODS

BACKGROUND

Ultraviolet (UV) light has shorter wavelengths than visible light. Ultraviolet light is emitted by the sun. In particular, the sun emits ultraviolet A ("UVA") radiation, ultraviolet B ("UVB") radiation, and ultraviolet C ("UVC") radiation. UVA radiation has longer wavelengths than UVB radiation or UVC radiation. UVA radiation, for instance, has wavelengths from 400 nm to 320 nm. UVB radiation, on the other hand, has wavelengths from 320 nm to 280 nm, while UVC radiation has wavelengths less than 280 nm.

Most of the ultraviolet radiation that passes through the Earth's atmosphere is UVA radiation. UVB radiation and UVC radiation, although smaller in presence, can be the most damaging to one's skin. For example, UVB radiation and UVC radiation have shorter wavelengths and therefore are the highest energy ultraviolet light. All forms of ultraviolet radiation, however, can be damaging to one's skin if left overexposed.

In the past, in order to protect oneself from the harmful effects of ultraviolet radiation, consumers have applied various sunscreens. Sunscreens, for instance, can be made with different Sun Protection Factor (SPF) values. The SPF values relate to the amount of protection that the sunscreen composition affords. SPF numbers, for instance, can range from as low as 2 to as high as 60. These numbers refer to the ability of the sunscreen product to screen or block out ultraviolet light, particularly UVA light. The SPF rating is calculated by comparing the amount of time needed to produce a sunburn on protected skin to the amount of time needed to cause a sunburn on unprotected skin. For example, ideally a person who applies sunscreen with an SPF value of 2 should be able to stay in the sun for twice as long without developing a sunburn. Similarly, if a person were to apply a sunscreen with an SPF value of 15, he/she should be able to remain exposed in the sun for 15 times longer before a sunburn develops.

Unfortunately, SPF values as applied to sunscreens are not always accurate. SPF values, for instance, do not always take into account the amount of B type or C type ultraviolet light present in the environment.

In view of the above, various manufacturers have recently developed ultraviolet sensors that are intended to help consumers monitor ultraviolet rays being admitted from the sun. Such UV sensors can, for instance, measure the amount of ultraviolet light present and provide a recommended exposure time based upon a person's skin type and/or the type of sunscreen that the person is using. For instance, the Chaney Instruments Company markets and sells a product called the UV Skin Care Sensor. The Vernier Software and Technology Company also markets and sells UVA sensors and UVB sensors.

The present disclosure is directed to further improvements in UV detection devices and is directed to further methods and products that are intended to assist consumers in preventing overexposure to UV radiation.

SUMMARY

In general, the present disclosure is directed to various different detection devices capable of measuring the amount of ultraviolet radiation in the environment. The devices, for instance, may be used by consumers to prevent against overexposure to ultraviolet rays. The present disclosure is also directed to various methods for monitoring ultraviolet radiation levels and for using the information to prevent against overexposure.

For example, in one embodiment, the present disclosure is directed to a portable UV detection apparatus that includes a skin type measuring device comprising a skin sensor. The skin type measuring device may be configured to determine at least one characteristic of a person's skin when the skin is placed next to the skin sensor. The at least one characteristic may comprise, in one embodiment, a determination of the color hue of the skin. Alternatively, the skin type measuring device may measure quantitatively the sensitivity of the skin to ultraviolet radiation. For example, in particular embodiments, the at least one characteristic may comprise an erythema measurement, a melanin measurement, or both.

The apparatus further includes a UV detection device comprising a UV sensor. The UV detection device is configured to measure an ultraviolet ray quantity present in an environment.

A controller is in communication with the skin type measuring device and the UV detection device. The controller, based on data received from the skin type measuring device and based on data received from the UV detection device, is configured to output information to a user regarding exposure to ultraviolet rays within the environment based on the measured skin type. For example, in one embodiment, the apparatus can include a display for communicating the output information. The output information may be in any suitable format. For example, the output information may include a recommended exposure time for the user in the environment. In fact, in one embodiment, the apparatus can further include a visual or audio alarm that produces a signal once the recommended exposure time has passed.

In general, any suitable skin type measuring device may be incorporated into the apparatus. For instance, the skin type measuring device may comprise a reflectance meter. In other embodiments, the skin type measuring device may comprise a reflectance spectrophotometer or a colorimetric instrument. In accordance with the present disclosure, the skin type measuring device, the UV detection device and the controller can be integrated together such that all of the components are contained in a single housing. The housing may include, for instance, a first window for making skin type measurements and a second window for making ultraviolet radiation measurements.

In one embodiment, the apparatus can further include an input panel that allows the user to input information into the apparatus for use by the controller. For example, the input panel may be used for a user to input a Sun Protection Factor value for a sunscreen the user has applied or is to apply to the skin. The information can then be used by the controller for calculating the recommended exposure time within the environment.

The UV detection device can be configured to measure different types of ultraviolet radiation. For instance, the UV detection device can be used to detect UVA radiation and UVB radiation. In one embodiment, for instance, the UV detection device may include a UVA sensor and a UVB sensor.

Another embodiment of the present disclosure is directed to a portable UV detection apparatus that also includes a UV detection device as described above. In this embodiment, however, the UV detection device is in communication with a light sensor that is configured to sense light rays in the environment. For instance, the light sensor may be configured to sense light rays at a particular wavelength which may include ultraviolet radiation. When a certain quantity of light has been sensed, the apparatus can be configured such that the UV detection device is activated and measures the ultraviolet ray quantity in the environment. The light sensor thus acts as a "switch" in activating the UV detection device should a minimum threshold of radiation be sensed in the environment. Once activated, the UV detection device may be configured to continuously monitor ultraviolet levels or monitor ultraviolet levels until the light sensor fails to sense light above a minimum threshold.

In an alternative embodiment, the light sensor senses light rays at a particular wavelength and emits a signal to a user. The user can then, based upon the information received from the light sensor, decide whether or not to activate the UV detection device in order to measure ultraviolet radiation.

In general, any suitable light sensor may be used in accordance with the present disclosure. For instance, in one embodiment, the light sensor may comprise a photosensor, an optical sensor, or a solar cell. When the light sensor is a solar cell, the light sensor may also be used to provide power to the apparatus.

In one embodiment, the apparatus can include an audible alarm that is activated when the light sensor activates the UV detection device. When incorporating a light sensor as described above, the apparatus is intended to remain exposed to the environment. In this regard, the apparatus can be attached to a wristband such that the apparatus can be worn like a watch. Alternatively, the apparatus can be mounted onto a hat or mounted onto a pair of sunglasses.

When the apparatus includes a light sensor, the light sensor may be used in conjunction with a skin type measuring device or may be used without the skin type measuring device depending upon the particular application.

Other features and aspects of the present disclosure are discussed in greater detail below.

BRIEF DESCRIPTION OF THE DRAWINGS

A full and enabling disclosure of the present disclosure, including the best mode thereof, directed to one of ordinary skill in the art, is set forth more particularly in the remainder of the specification, which makes reference to the following figures.

Figure 1:
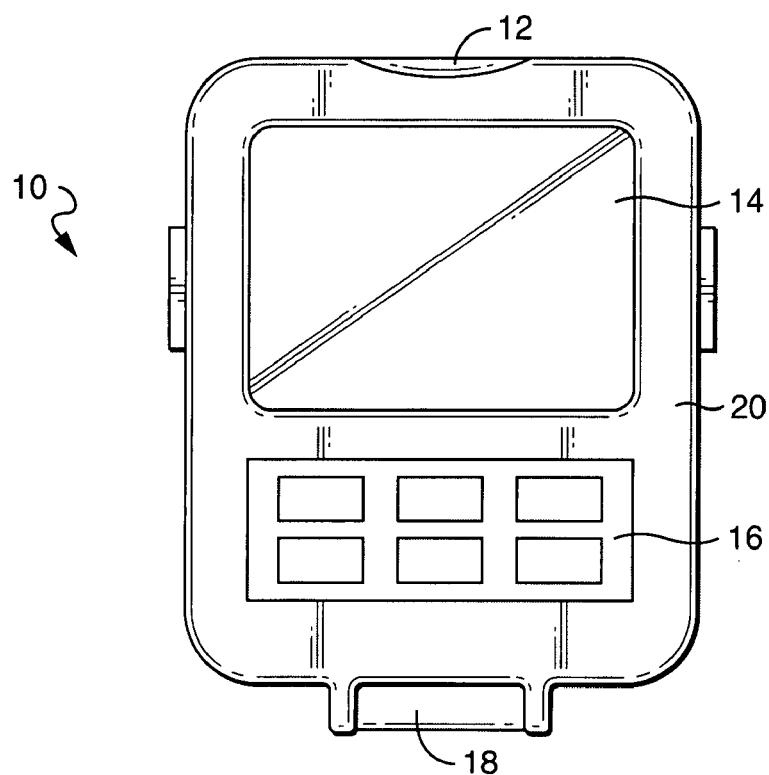
FIG. 1 is a plan view of one embodiment of a UV detection apparatus made in accordance with the present disclosure.

Repeat use of reference characters in the present specification and drawings is intended to represent same or analogous features or elements of the disclosure.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to various devices and methods for monitoring ultraviolet radiation in an environment. The devices can be used, for instance, by consumers to prevent against overexposure. Overexposure to ultraviolet radiation, for instance, can lead to sunburns and ultimately to more serious health problems, such as skin cancer. In fact, ultraviolet exposure is listed as a known carcinogen by the National Cancer Institute.

In one embodiment, for instance, the present disclosure is directed to a portable UV detection apparatus that integrates a skin type measuring device with an ultraviolet detection device. Various advantages and benefits can be obtained by integrating a skin type measuring device and a UV detection device into a single apparatus. For example, when determining overexposure to ultraviolet radiation a person's skin type is one factor that should be considered. The skin type measuring device can be any suitable device that measures at least one characteristic of a person's skin. Once the characteristic is measured, the UV detection device may be calibrated or otherwise used in conjunction with the skin type measurement to provide output information to the user regarding exposure to ultraviolet radiation within the environment.

Of particular advantage, the skin type measuring device can be used over a period of time in order to track changes in a person's skin as the skin begins to tan as a result of exposure to the sun. This information may then be used to tune recommended exposure limits in a personalized manner taking into account the amount of ultraviolet radiation exposure and the resulting changes to the skin.

In the past, various different ultraviolet radiation sensors have been proposed. For example, various ultraviolet sensors are disclosed in U.S. Pat. No. 4,962,910, U.S. Pat. No. 5,365,068, U.S. Pat. No. 6,936,824, and U.S. Patent Application Publication No. 2004/0031927, which are all incorporated herein by reference. The UV sensors described in the above references, for instance, monitor ultraviolet radiation and can allow for the input of various information in order to assist consumers in preventing against overexposure.

In the above references, however, skin type, if it was considered at all, was estimated by the person using the UV sensor. For instance, some of the devices may include a manner of inputting a person's skin type. The skin types may include, for instance, the following categories: (1) fair skin, always burns easily and never tans; (2) fair skin, always burns easily and tans minimally; (3) light brown skin that burns moderately and tans gradually; (4) moderate brown skin that burns minimally and always tans well; (5) dark brown skin that rarely burns and tans profusely; and (6) dark brown skin that never burns and is deeply pigmented. In prior art devices, it was up to the consumer to classify his/her skin and then input this information into the UV sensor for determining a maximum exposure value. As can be readily discerned from the above categories, however, the inputted skin type determination was subjective. For the sensors to provide reliable information, the sensor had to rely on consumers to accurately classify their own skin.

According to the present disclosure, however, the apparatus is capable of automatically and quantitatively measuring at least one characteristic of a person's skin that is used in conjunction with the UV detection device for determining maximum exposure limits. The apparatus of the present disclosure thus can more accurately and precisely measure a person's skin type and/or sensitivity for providing more reliable information regarding ultraviolet radiation exposure. In addition, the skin type measuring device can be used to monitor changes in a user's skin as the skin tans or becomes sunburn.

For example, referring to FIG. 1, one embodiment of a portable UV detection apparatus generally 10 made in accordance with the present disclosure is illustrated. As shown, the UV detection apparatus 10 includes an ultraviolet radiation sensor 12, a visual and/or audible display 14, an input panel 16, and a skin type sensor 18 all contained in a single housing 20.

Figure 3:
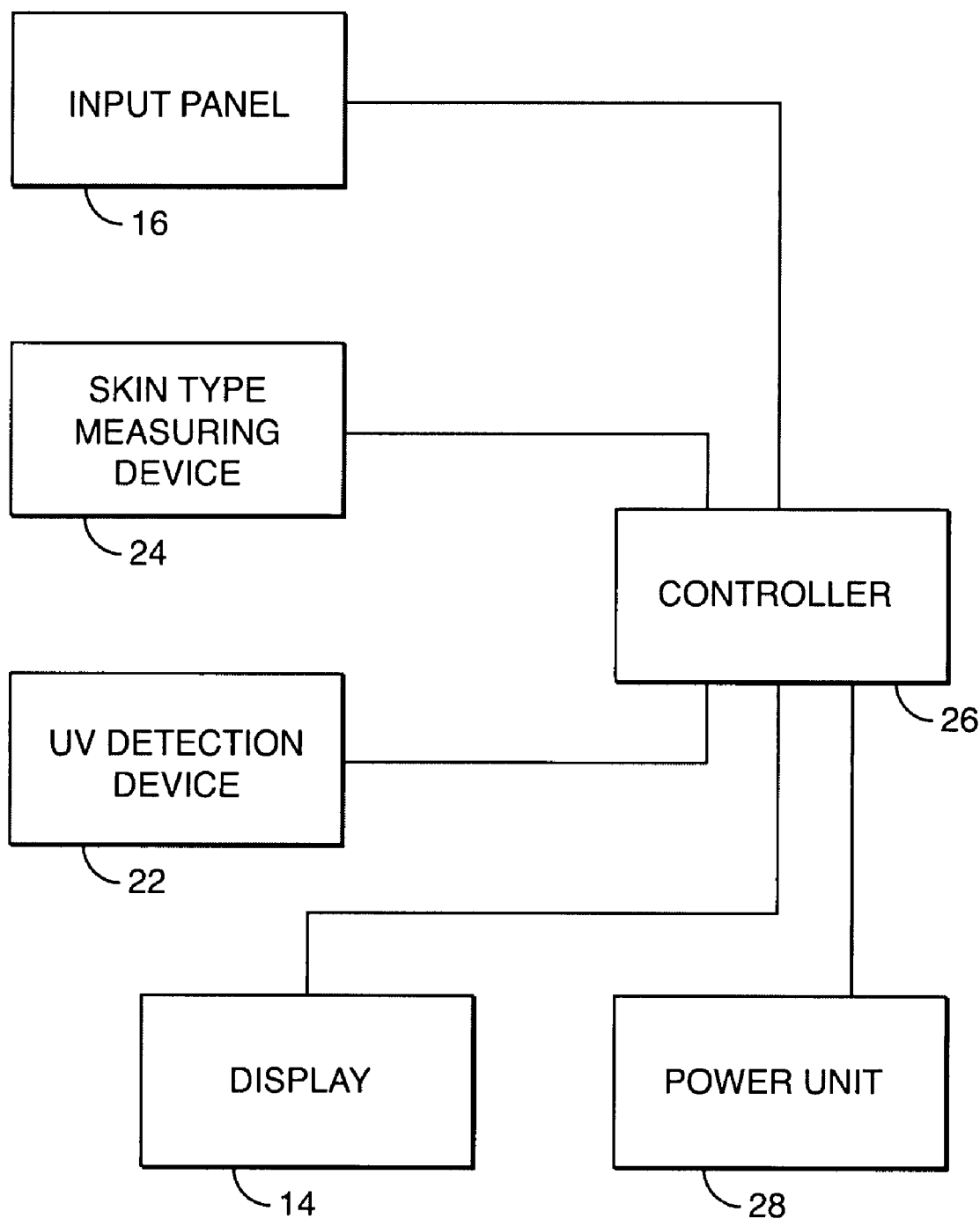
FIG. 3 is a diagram of one embodiment of a system in accordance with the present disclosure.

Referring to FIG. 3, one embodiment of a diagram of the system contained within the housing 20 is shown. For example, the UV sensor 12 as shown in FIG. 1 can be part of a UV detection device 22 as shown in FIG. 3. Similarly, the skin type sensor 18 can be part of a skin type measuring device 24 as shown in FIG. 3. As also illustrated in FIG. 3, the skin type measuring device 24 and the UV detection device 22 can be in communication with a controller 26. The controller 26 can also receive input from the input panel 16 and thereafter send information to the display 14. The controller 26, for instance, can be any suitable programmable logic unit, such as a microprocessor.

As shown in FIG. 3, the system further includes a power unit 28. The power unit 28 is for providing power or energy to all of the electronic devices for operation of the apparatus. The power unit may comprise, for instance, any suitable source of DC power. The power unit 28, for instance, may comprise batteries such as rechargeable batteries or may comprise a solar cell.

In order to operate the UV detection apparatus 10 as shown in FIG. 1, a user initially scans his skin with the skin type sensor 18. The skin type sensor and the skin type measuring device are configured to measure at least one characteristic of the skin of the user.

Skin color is predominantly determined by pigments such as hemoglobin, melanin, bilirubin, and carotene. Melanin, for instance, is one of the primary determinants of human skin color. Melanin also protects the skin from solar ultraviolet radiation. In particular, greater amounts of melanin in the skin generally suggests less sensitivity to UV radiation.

When a person is overexposed to solar radiation, the person can develop erythema. Erythema is an abnormal redness of the skin caused by capillary congestion.

The skin type measuring device of the present disclosure can measure any suitable characteristic of the skin that provides an indication of the ability of the skin to be subjected to ultraviolet radiation. In one embodiment, for instance, the skin type measuring device may be simply used to measure the color hue of a person's skin. In other embodiments, the skin type measuring device may be configured to particularly measure melanin levels in the skin and/or an erythema level of the skin. In one particular embodiment, melanin levels and erythema levels may both be measured.

Ultimately, the skin type measuring device may be configured to quantitatively determine the sensitivity of the skin to ultraviolet radiation.

Depending upon the application, a user can take a single reading of his/her skin or may take multiple readings. For example, in one embodiment, skin type measurements may be taken over different parts of the body. The apparatus can be configured to average the different measurements together or to only use the skin type measurement that is the fairest or the most susceptible to becoming sunburned.

In an alternative embodiment, the apparatus may be configured to be worn against a user's skin. In this embodiment, the skin type measuring device may take continuous readings or readings periodically in order to take into account changes to the skin as the skin remains exposed to the sun.

In general, any suitable skin type measurement device may be used. For example, in one embodiment, the skin type measurement device may comprise a reflectance meter. For instance, the skin type measurement device may comprise a scanning reflectance spectrophotometer, a colorimetric instrument, or a chromameter. Suitable reflectance meters that may be incorporated in the apparatus, for instance, are commercially available from the Minolta Company.

In an alternative embodiment, the skin type measurement device may comprise the skin tone measurement device disclosed in U.S. Patent Application Publication No. 2006/0210154, which is incorporated herein by reference. The skin tone measurement device disclosed in the '154 application, for instance, includes a skin sensor that comprises a window through which light is emitted onto the skin. The skin sensor further includes a detection window configured to receive the light emitted through the outlet window. The light emitted by the skin type sensor may originate, for instance, from a light emitting diode.

In yet another alternative embodiment, the skin type measurement device may comprise an absorbance measuring device that includes a broadband sensor. The sensor, for instance, may determine the incident UV radiation and then compare it to the reflected UV radiation in order to determine the absorbed UV radiation.

The one or more measurements taken by the skin type measuring device 24 as shown in FIG. 3 are then sent to the controller 26 for processing.

In addition to sensing a person's skin type, the apparatus also records the amount of ultraviolet radiation present in the environment using the UV sensor 12 and the UV detection device 22. In general, any suitable UV detection device may be incorporated into the apparatus. The UV detection device, for instance, may comprise any of the devices disclosed in U.S. Pat. No. 4,962,910, U.S. Pat. No. 5,365,068, U.S. Pat. No. 6,936,824 and in U.S. Patent Application Publication No. 2004/0031927.

The UV detection device may be configured to measure all types of ultraviolet radiation present within the environment. For instance, the UV detection device can be configured to measure UVA levels, UVB levels, and/or UVC levels.

In one embodiment, the apparatus can include multiple UV sensor and/or UV detection devices. Each sensor or device, for instance, may measure a particular type of ultraviolet radiation. For example, in one embodiment, the apparatus can include a first UV sensor for sensing UVA radiation and a second sensor for measuring UVB radiation.

The one or more UV radiation measurements can then be sent to the controller 26 as shown in FIG. 3. Although optional, the apparatus 10 can further include the input panel 16 for providing further information to the controller 26. The input panel 16, for instance, can be used to receive further information from the user regarding the conditions of exposure. For example, in one embodiment, the input panel can be configured to receive the Sun Protection Factor (SPF) value of a sunscreen that the user is applying to the skin in the environment in which the apparatus is to be used. The input panel can also receive various other information. For instance, if desired, the apparatus can be configured to receive user inputted skin type information that may be used in conjunction with the skin type measurements made by the skin type measuring device. For instance, the input panel can be configured to receive one of the six skin types as described above.

In addition to the above information, it should be understood that the input panel 16 may be configured to accept any other information that may be helpful in determining exposure limits for a user. Other information that can be added may include, for instance, age, sex, whether the user will be in direct sunlight or in the shade and whether the user will be surrounded by highly reflective surfaces, such as water or snow.

Once all the appropriate measurements have been taken and all of the appropriate information has been entered through the input panel 16, the controller 26 is configured to use the data to provide information to a user regarding ultraviolet radiation exposure within the environment. The controller 26, for instance, can output various helpful recommendations and other information via the display 14. For example, in one embodiment, the controller 26 can be configured to calculate a recommended exposure time for the user within the environment that will prevent again sunburns and other harmful effects due to ultraviolet radiation. In fact, in one embodiment, the apparatus can include a visual and/or audible alarm that is activated once the recommended time has past.

In an alternative embodiment, the controller can be configured to output not only a recommended exposure time within the environment but also a recommended minimum SPF value for a sunscreen that the user should apply to his/her skin. In another embodiment, the apparatus may be configured so that the user can input the amount of time he/she will be in the environment and the controller will output a recommended SPF value for a sunscreen to apply.

Figure 2:
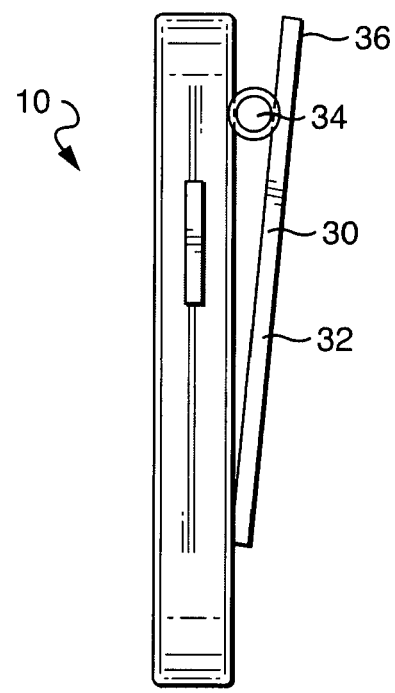
FIG. 2 is a side view of the apparatus shown in FIG. 1.

Referring to FIG. 2, one embodiment of a side view of the apparatus 10 as shown in FIG. 1 is illustrated. As shown in FIG. 2, the apparatus 10 includes an attachment device 30 for attaching the device to any suitable adjacent structure. As shown, the attachment device 30 includes a clamping plate 32 that pivots along a pivot point 34. The pivot point 34, for instance, may include a spring that biases the clamping plate 32 towards the back of the apparatus. In this manner, an end 36 of the clamping plate 32 can be pressed upon by the user in order to place the clamping plate on any suitable adjacent structure for attaching the apparatus thereto.

The attachment device 30, for instance, can be used to temporarily attach the UV detection apparatus to any suitable structure. For instance, the attachment device can be used to clip the apparatus to a beach bag, to one's clothing, to a hat, to an umbrella, to a chair, or the like. It should also be understood that any suitable attachment device may be incorporated into the apparatus. For instance, in other embodiments, the attachment device may comprise an adhesive, a strap such as a wristband, or the like.

In other embodiments, the UV detection apparatus 10 may not include an attachment device but, instead, may be incorporated directly into a product. For instance, the UV detection apparatus may be incorporated into a chair or into an article of clothing.

Figure 4:
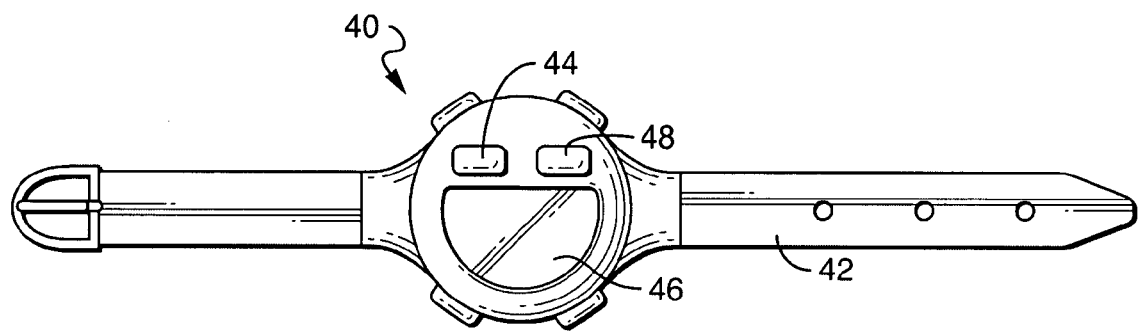
FIG. 4 is a plan view of still another embodiment of a UV detection apparatus made in accordance with the present disclosure.

Referring to FIG. 4, another embodiment of a portable UV detection apparatus 40 is shown. In this embodiment, the UV detection apparatus generally has the shape of a wristwatch and can be attached to a user's wrist using the wristband 42. A wristband, or body worn device could effectively measure the skin type automatically as it is worn. In this embodiment, the UV detection apparatus 40 includes a UV sensor 44 that represents part of a UV detection device similar to the embodiment illustrated in FIG. 1. The apparatus 40 further includes a display 46 for communicating information to a user. In this embodiment, the apparatus 40 further includes a light sensor 48. The light sensor 48 monitors the amount of light at, for instance, a particular wavelength and acts as a switch to activate the UV detection device should the amount of light sensed by the light sensor increase above a predetermined threshold. For example, the light sensor may be configured to sense ultraviolet light. When quantities of the ultraviolet light are above a certain amount, the UV detection device may be activated for automatically measuring ultraviolet radiation within the environment.

As the apparatus 40 begins to sense the amount of ultraviolet radiation present within the environment, there is no feedback required by the user other than an initial setup of the device. Periodic or continuous monitoring of the ultraviolet radiation present in the environment can be relayed to the user of the device. Continuous monitoring of the apparatus allows for time spent in the shade but still measures any reflected ultraviolet radiation present that may be incident on the user for adjusting the exposure time accordingly.

The light sensor 48 can be any suitable light sensing device. For example, in one embodiment, the light sensor 48 comprises an optical sensor. In still another embodiment, the light sensor 48 comprises a photosensor. In yet another embodiment, the light sensor 48 comprises a solar cell. When a light sensor comprises a solar cell, the solar cell may also be used to provide power to the apparatus.

In the embodiment illustrated in FIG. 4, the apparatus 40 may also include a controller in communication with the light sensor 48 and the UV detection device. The controller can be configured to tailor a certain output that is to be communicated on the display 46. For instance, in one embodiment, the display 46 may indicate to the user a recommended maximum exposure time in the environment. In other embodiments, however, the apparatus 40 may simply communicate to the user the amount of ultraviolet radiation being measured at any given point in time. For instance, the display 46 may display the amount of UVA radiation, the amount of UVB radiation and/or the amount of UVC radiation being measured. In this regard, the apparatus 40 may include appropriate UV sensors and detection devices to make the appropriate measurements.

In one embodiment, the apparatus shown in FIG. 1 may be similar to the apparatus 40 illustrated in FIG. 4 with the inclusion of the light sensor 48.

Figure 5:
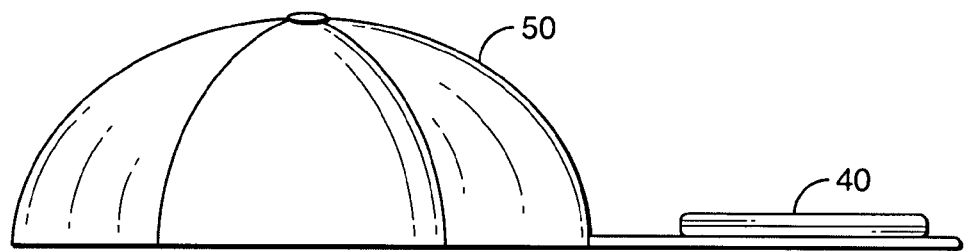
FIG. 5 is a side view of one embodiment of a hat incorporating a UV detection apparatus in accordance with the present disclosure.

The UV detection apparatus 40 as shown in FIG. 4 may be incorporated into various different products in addition to a wristwatch-like product as shown in FIG. 4. For instance, referring to FIG. 5, the UV detection apparatus 40 is shown mounted onto a hat 50. In addition, it should be understood that the UV detection apparatus 40 may be mounted onto any suitable article of clothing. Other products that may incorporate the UV detection apparatus 40 include bicycles, bracelets, sunscreen bottles, beach balls, hat clips, beach towels, coolers and other beverage containers, umbrellas, outdoor furniture, tents, hiking equipment, and the like.

Figure 6:
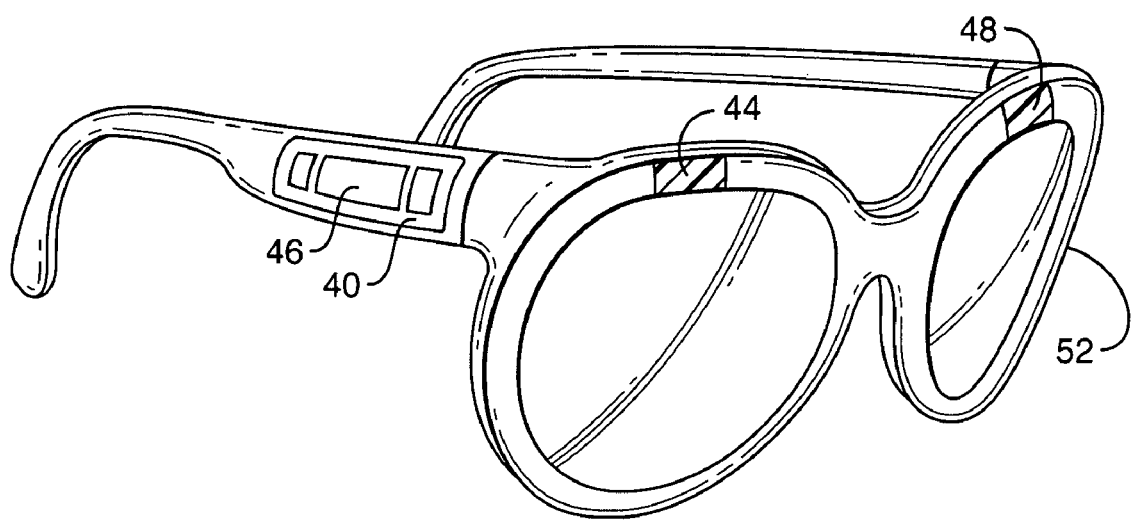
FIG. 6 is a perspective view of a pair of sunglasses incorporating a UV detection apparatus in accordance with the present disclosure.

Referring to FIG. 6, in one embodiment, the UV detection apparatus 40 may be incorporated onto a pair of glasses 52, such as a pair of sunglasses. As shown, in this embodiment, the sunglasses 52 include at least one UV sensor 44 and a light sensor 48. The UV detection apparatus 40 can further include a display 46 for communicating information regarding the amount of ultraviolet radiation present in the environment to the user.

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged either in whole or in part. Furthermore, those of ordinary skill in the art will appreciate that the foregoing description is by way of example only, and is not intended to limit the disclosure so further described in such appended claims.

What is claimed is:

1. A portable UV detection apparatus comprising:
    a skin type measuring device comprising a skin sensor, the skin type measuring device being configured to determine at least one characteristic of a person's skin when the skin is placed adjacent to the skin sensor wherein the at least one characteristic of a person's skin determined by the skin type measuring device comprises both an erythema measurement and a melanin measurement wherein the skin type measuring device determination is based, at least in part, on determining an amount of ambient ultraviolet radiation present in an environment to which the person's skin is exposed and comparing this to an amount of the ambient ultraviolet radiation reflected from the person's skin;

a UV detection device comprising a UV sensor, the UV detection device being configured to measure an ultraviolet ray quantity present in an environment; and a controller in communication with the skin type measuring device and the UV detection device, the controller, based on data received from the skin type measuring device, data received from the UV detection device as well as data from a user including the length of time the user will be exposed to the environment, being configured to output a suggested skin protective measure to the user based upon the length of time the user will be exposed to ultraviolet rays within the environment.

2. A portable UV detection apparatus as defined in claim 1, wherein the skin type measuring device, the UV detection device and the controller are integrated together such that they are all contained in a single housing.

3. A portable UV detection apparatus as defined in claim 1, wherein the skin type measuring device comprises a reflectance meter.

4. A portable UV detection apparatus as defined in claim 1, further comprising a display that communicates the output information to a user.

5. A portable UV detection apparatus as defined in claim 1, wherein the output information comprises a recommended exposure time for the user in the environment.

6. A portable UV detection apparatus as defined in claim 5, wherein the apparatus further comprises a visual or audio alarm that is activated once the recommended exposure time has passed.

7. A portable UV detection apparatus as defined in claim 1, wherein the UV detection device measures ultraviolet A rays and ultraviolet B rays.

8. A portable UV detection apparatus as defined in claim 1, further comprising an attachment device for attaching the apparatus to an adjacent structure.

9. A portable UV detection apparatus as defined in claim 1, further comprising an input panel that allows a user to input a Sun Protection Factor value for a sunscreen, the controller being configured to receive the inputted Sun Protection Factor value and output the information to a user regarding exposure to ultraviolet rays within the environment.

10. A portable UV detection apparatus as defined in claim 1, wherein the output information generated by the controller includes a recommended sunscreen to apply to the skin having a minimum recommended Sun Protection Factor value.

11. A portable UV detection apparatus as defined in claim 1, wherein the at least one characteristic determined by the skin type measuring device comprises a color hue of a person's skin.

12. A portable UV detection apparatus as defined in claim 1, wherein the at least one characteristic determined by the skin type measuring device comprises a sensitivity of a person's skin to ultraviolet radiation exposure.

13. A portable UV detection apparatus as defined in claim 1, wherein the UV detection device is configured to continuously measure ultraviolet ray quantities present in an environment.

14. A portable UV detection apparatus as defined in claim 1, wherein the apparatus further includes a solar cell for powering the apparatus.

15. A portable UV detection apparatus comprising:

a UV detection device comprising a UV sensor, the UV detection device being configured to measure an ultraviolet ray quantity present in an environment; and a light sensor configured to sense light rays in the environment, the light sensor being in communication with the UV detection device;

wherein when the light sensor senses that an amount of ultraviolet light is above a minimum threshold, the UV detection device is activated and measures the ultraviolet ray quantity in the environment; and a skin type measuring device comprising a skin sensor the skin type measuring device being configured to determine a user's skin type and at least one characteristic of the user's skin when the skin is placed adjacent to the skin sensor wherein the at least one characteristic of the user's skin determined by the skin type measuring device comprises both an erythema measurement and a melanin measurement wherein the skin type measuring device determination is based, at least in part, on determining an amount of ambient ultraviolet radiation present in an environment to which the user's skin is exposed and comparing this to an amount of the ambient ultraviolet radiation reflected from the user's skin.

16. A portable UV detection apparatus as defined in claim 15, wherein, when a certain quantity of light has been sensed by the light sensor, the detection apparatus is configured to send a signal to a user.

17. A portable UV detection apparatus as defined in claim 15, wherein the apparatus is attached to an article of clothing.

18. A portable UV detection apparatus as defined in claim 15, wherein the apparatus includes an audible alarm that emits an audible signal when the UV detection device is activated.

19. A portable UV detection apparatus as defined in claim 15, wherein the apparatus further includes a controller in communication with the UV detection device, the controller, based on data received from the UV detection device, being configured to output information to a user regarding exposure to ultraviolet rays within the environment.

20. A portable UV detection apparatus as defined in claim 19, wherein the output information comprises a recommended exposure time for the user in the environment.

21. A portable UV detection apparatus as defined in claim 15, wherein the UV detection device measures ultraviolet A rays and ultraviolet B rays.

22. A portable UV detection apparatus as defined in claim 15, wherein the light sensor comprises a solar cell, a photo sensor, or an optical sensor.

23. A portable UV detection apparatus as defined in claim 15, wherein the apparatus is attached to a wristband or mounted onto a pair of sunglasses.

24. A portable UV detection apparatus as defined in claim 15, wherein the UV detection device includes a first UV sensor and a second UV sensor, the first UV sensor being configured to sense ultraviolet A rays, while the second UV sensor is configured to sense ultraviolet B rays.

* * * * *